(12) United States Patent
Boyd et al.

(10) Patent No.: US 8,226,631 B2
(45) Date of Patent: Jul. 24, 2012

(54) DRIVE MECHANISMS SUITABLE FOR USE IN DRUG DELIVERY DEVICES

(75) Inventors: Malcolm Boyd, Leamington (GB);
Richard Letham, Kingston Upon Thames (GB); David Plumptre, Droitwich (GB); Robert Veasey, Warwick (GB); James May, Coventry (GB)

(73) Assignee: Sanofi Aventis Deutschland GmbH, Frankfurt am Main (DE)

( * ) Notice: Subject to any disclaimer, the term of this patent is extended or adjusted under 35 U.S.C. 154(b) by 114 days.

(21) Appl. No.: 12/466,590

(22) Filed: May 15, 2009

(65) Prior Publication Data
US 2010/0094253 A1  Apr. 15, 2010

Related U.S. Application Data

(63) Continuation of application No. PCT/EP2007/009675, filed on Nov. 8, 2007.

(30) Foreign Application Priority Data

Nov. 17, 2006  (EP) .................................. 06023955

(51) Int. Cl.
*A61M 31/00* (2006.01)
(52) U.S. Cl. ........ 604/506; 604/207; 604/208; 604/209; 604/211; 604/181
(58) Field of Classification Search .................. 604/209, 604/201, 211, 181, 110, 207, 208, 506
See application file for complete search history.

(56) References Cited

U.S. PATENT DOCUMENTS

| 4,592,745 | A | 6/1986 | Rex et al. |
| 6,221,053 | B1 * | 4/2001 | Walters et al. ............. 604/211 |
| 2004/0210199 | A1 | 10/2004 | Atterbury et al. |
| 2004/0267207 | A1 * | 12/2004 | Veasey et al. ............ 604/208 |

FOREIGN PATENT DOCUMENTS

| WO | 99/38554 A1 | 8/1999 |
| WO | 01/89613 A1 | 11/2001 |
| WO | 02/053214 A1 | 7/2002 |
| WO | 2004/078239 A1 | 9/2004 |
| WO | 2006/024461 A1 | 3/2006 |
| WO | 2006/089768 A1 | 8/2006 |
| WO | 2008/058667 A1 | 5/2008 |

OTHER PUBLICATIONS

International Search Report Form PCT/ISA/210 (second sheet) (Apr. 2005)—PCT/EP2007/009675, pp. 1-5.

* cited by examiner

*Primary Examiner* — Bhisma Mehta
*Assistant Examiner* — Edelmira Bosques
(74) *Attorney, Agent, or Firm* — McDonnell Boehnen Hulbert & Berghoff LLP

(57) ABSTRACT

The present invention relates to drive mechanisms suitable for use in drug delivery devices, in particular pen-type injectors, wherein a number of pre-set doses of medicinal product can be administered. In particular, the present invention relates to such drug delivery devices where a user may activate the drug delivery device.

15 Claims, 3 Drawing Sheets

DRIVE MECHANISMS SUITABLE FOR USE IN DRUG DELIVERY DEVICES

THE TECHNICAL FIELD OF THE INVENTION

The present invention relates to drive mechanisms suitable for use in drug delivery devices, in particular pen-type injectors, wherein a number of pre-set doses of medicinal product can be administered. In particular, the present invention relates to such drug delivery devices where a user may activate the drug delivery device.

DESCRIPTION OF RELATED ART

Such drug delivery devices have application where persons without formal medical training, i.e., patients, need to administer an accurate and predefined dose of a medicinal product, such as heparin or insulin. In particular, such devices have application where medicinal product is administered on an irregular basis over a short-term or long-term period.

These circumstances set a number of requirements for drug delivery devices of this kind. The device must be robust in construction, yet easy to use in terms of the manipulation of the parts, understanding by a user of its operation and the delivery of the required dose of medicament. Dose setting must be easy and unambiguous. Where the device is to be disposable rather than reusable, the device should be cheap to manufacture and easy to dispose of (preferably being suitable for recycling). To meet these requirements the number of parts required to assemble the device and the number of material types the device is made from need to be kept to a minimum.

User operated drug delivery devices are well known within the medical field.

U.S. Pat. No. 6,048,336 discloses an injection device wherein a pre-selected set medicinal dose to be administered is selected by means of a rotatable dosing element. Once the dose has been set, an end member is pulled axially away from the remainder of the pen base until a stop is reached. A dose is dispensed by the end member being axially driven towards the pen base in turn driving an internal plunger-engaging member. Whilst this device provides a useful embodiment for administering a pre-set dose the intuitiveness of setting a pre-set dose remains unsolved as two actions need to be performed to arm the device.

WO 2004/078239 A1 teaches a medication dispensing apparatus having a rotating drive sleeve and dose dial sleeve with a clutch element located between the drive sleeve and dose dial sleeve to allow independent rotation between the drive sleeve and the dose dial sleeve.

In WO 2003/020347 A2 a medication dispensing apparatus is divulged having an axially moving actuator that is pulled out of the device body to set a dose and pushed into the body to dispense the set dose, having a clutch element with a number of prongs used to selectively transmit motion of the actuator member to the drive member.

Surprisingly it was found that the drive mechanism according to instant invention without having a clutch element provides a valuable technical alternative for drive mechanisms, wherein reduced force is needed to actuate the mechanism. This is achieved by the introduction of a piston rod as defined by instant invention. Further the drive mechanism according to instant invention further provides the advantage of intuitive and easy to use dose setting.

DESCRIPTION OF THE INVENTION

According to a first aspect of the present invention, a drive mechanism for use in a drug delivery device is provided comprising:

a housing having a helical thread, preferably an internal helical thread;
an activation means that is non-rotatable with respect to the said housing;
a drive sleeve engaged with the said housing;
a piston rod engaged with the said drive sleeve and said housing;
characterized in that,
a) when the said activation means moves proximally with respect to the said housing the said drive sleeve rotates with respect to the said activation means and moves proximally with respect to the said housing;
b) when the said activation means moves distally with respect to the said housing the said drive sleeve moves distally with respect to the said housing and is prevented from rotating with respect to the said housing and the said piston rod is caused to rotate with respect to the said housing so that a force is transferred in the longitudinal direction to the distal end of the drug delivery device.

In a preferred embodiment of the drive mechanism of instant invention the piston rod is of essentially circular cross-section.

In another preferred embodiment of the drive mechanism of instant invention the piston rod further comprises a distal threaded portion and a proximal threaded portion wherein the said distal threaded portion and the said proximal threaded portion are oppositely disposed.

In a further preferred embodiment of the drive mechanism of instant invention the drive sleeve is coupled with the said activation means for longitudinal travel and relative rotation between the said drive sleeve and the said activation means is allowed.

The term "drug delivery device" according to instant invention shall mean a single-dose or multi-dose or pre-set dose or pre-defined dose, disposable or re-useable device designed to dispense a user selectable or pre-defined dose of a medicinal product, preferably multiple pre-defined doses, e.g. insulin, growth hormones, low molecular weight heparins, and their analogues and/or derivatives etc. Said device may be of any shape, e.g. compact or pen-type. Dose delivery may be provided through a mechanical (optionally manual) drive mechanism or electrical drive mechanism or electro-mechanical mechanism or stored energy drive mechanism, such as a spring, etc. Dose selection may be provided through a manual mechanism or electro-mechanical mechanism or electronic mechanism. Additionally, said device may contain components designed to monitor physiological properties such as blood glucose levels, etc. Furthermore, the said device may comprise a needle or may be needle-free. In addition, the said device may comprise a fixed needle or a replaceable needle or a moving needle or a shielded moving needle. In particular, the term "drug delivery device" shall mean a disposable needle-based pen-type device providing multiple pre-defined doses having mechanical and manual dose delivery and dose selection mechanisms, which is designed for use by persons without formal medical training such as patients. Preferably, the drug delivery device is of the injector-type.

The term "housing" according to instant invention shall preferably mean any exterior housing ("main housing", "body", "shell") or interior housing ("insert", "inner body") having one or more helical threads. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge, which may be replaceable or non-replaceable, from which a number of doses of a medicinal product may by dispensed.

In a more specific embodiment of instant invention, the housing is provided with a plurality of maximum dose stops adapted to be abutted by a radial and/or axial stop provided on the activation means.

The term "engaged" according to instant invention shall particularly mean the interlocking of two or more components of the drive mechanism/drug delivery device, e.g. a spline, thread, or meshed teeth connection, preferably the interlocking of helical threads of components ("threadedly engaged").

The term "coupled" according to instant invention shall mean the connection of two or more components of the drive mechanism/drug delivery device, e.g. using a flange or the like, in which the degree of freedom of the components with respect to each other is limited. In a preferred embodiment one component is permitted to rotate around one axis with respect to another component and is limited from all other rotational and/or translational movement with respect to another component.

In a more particular embodiment of instant invention, the drive sleeve is provided with a flange that is coupled to the activation means such that relative rotation about the main longitudinal axis of the drug delivery device is permitted but all other relative movement is essentially prevented.

The term "drive sleeve" according to instant invention shall mean any essentially tubular component of essentially circular cross-section and which is further releasibly connected to the dose dial sleeve. In a preferred embodiment the drive sleeve is further engaged with the piston rod.

In a more particular embodiment of instant invention, the drive sleeve is provided at a distal end with first and second flanges with an intermediate helical thread between the first and second flanges, having a nut disposed between the first and second flanges and keyed to the housing by spline means. Optionally, a first radial stop may be provided on a proximal face of the nut and a second radial stop may be provided on a distal face of the second flange.

The term "piston rod" according to instant invention shall mean a component adapted to operate through/within the housing, designed to translate axial movement through/within the drug delivery device, preferably from the drive sleeve to the piston, for the purpose of discharging/dispensing an injectable product. Said piston rod may be flexible or not. It may be a simple rod, a lead-screw, a rack and pinion system, a worm gear system, or the like. It may further be of a unitary or multi-component construction. The term "piston rod" shall further mean a component having a circular or non-circular cross-section. It may be made of any suitable material known by a person skilled in the art.

In a preferred embodiment, the piston rod comprises at least one, more preferably two, external and/or internal helical threads. In another preferred embodiment of the piston rod according to instant invention, a first helical thread is located at the distal end and a second helical thread is located at the proximal end of the said piston rod, whereby the said threads may have the same or, preferably, opposite dispositions. In another preferred embodiment the piston rod of instant invention comprises threads having the same leads at the proximal and the distal end.

In yet another preferred embodiment of instant invention the lead of the second helical thread of the piston rod shall be greater than the lead of the first helical thread. More preferred, the ratio of the leads of the helical threads of the said first and the said second helical threads is 1:1 to 1:20, even more preferred 1:1 to 1:10, most preferred 1:2. Preferably, one of the said threads is designed to engage with the drive sleeve.

The term "activation means" according to instant invention shall mean any component designed to transmit force from the user to the drive sleeve. Preferably the term "activation means" shall mean a component that does not rotate with respect to the housing but is allowed to move longitudinally with respect to the housing to transmit force from the user to the drive sleeve. In a more preferred embodiment of instant invention the activation means is provided with grip surfaces at the proximal end to enable the user to activate the device. In yet another preferred embodiment of instant invention the activation means is provided with a contact surface to allow the user to dispense a selected dose of medicament.

The term "graphical status indicator" according to instant invention shall preferably mean any markings, symbols, numerals, etc., e.g. printed on the external surface of a component of the device, for example the drive sleeve or an odometer or a dose dial sleeve or an activation means, or the like, preferably the activation means, for indicating to the user when the device has been activated and/or is in operation and/or direction of operation and/or a dose of medicament has been delivered.

The "proximal end" of the device or a component of the device shall mean the end, which is furthest away from the dispensing end of the device.

The "distal end" of the device or a component of the device shall mean the end, which is closest to the dispensing end of the device.

A second aspect of instant invention provides an assembly for use in a drug delivery device comprising the drive mechanism according to instant invention.

A third aspect of the present invention provides a drug delivery device comprising the drive mechanism or the assembly according to instant invention.

A fourth aspect of the present invention provides a method of assembling a drug delivery device comprising the step of providing a drive mechanism or an assembly according to instant invention.

A fifth aspect of instant invention is the use of a drug delivery device according to instant invention for dispensing a medicinal product preferably dispensing a pharmaceutical formulation (e.g. solution, suspension etc.) comprising an active compound selected from the group consisting of insulin, growth hormone, low molecular weight heparin, their analogues and their derivatives.

BRIEF DESCRIPTION OF THE DRAWINGS

Without any limitation, the instant invention will be explained in greater detail below in connection with a preferred embodiment and with reference to the drawings in which.

DETAILED DESCRIPTION OF THE EMBODIMENT

Figure 1:
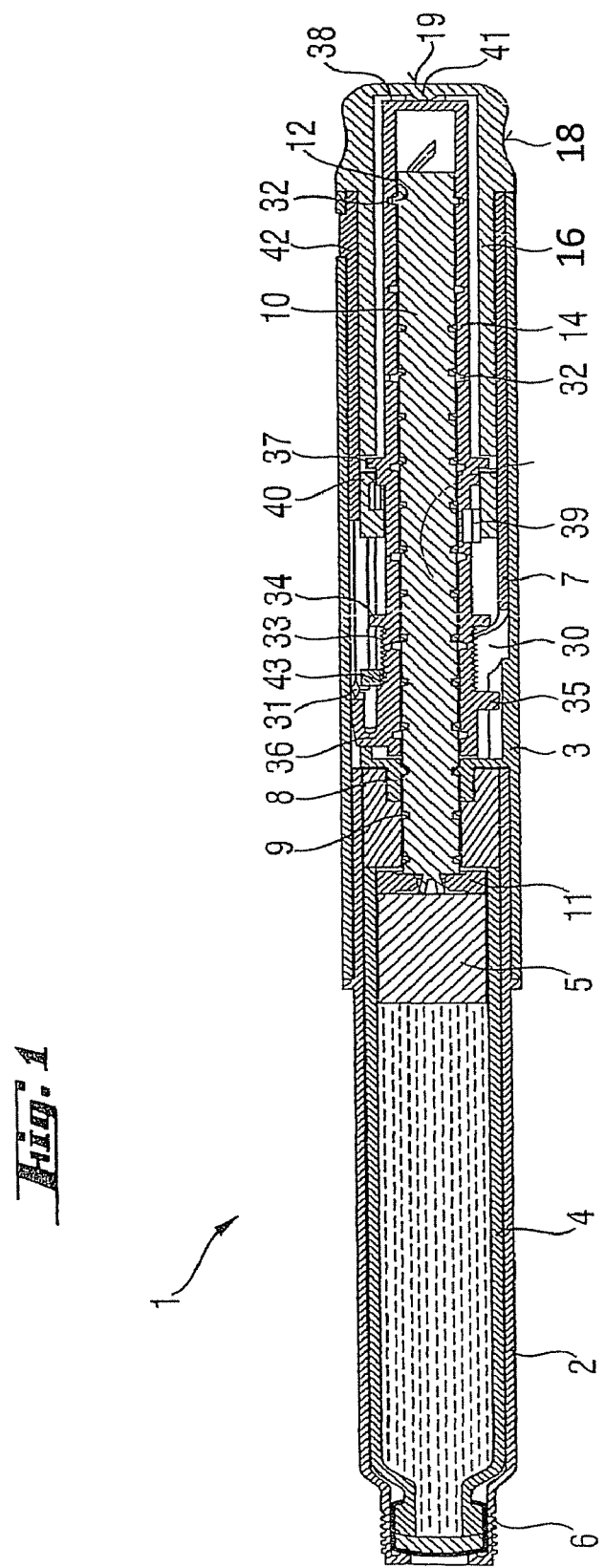
FIG. 1; shows a sectional view of an embodiment of the drug delivery device in accordance with the present invention in a first, cartridge full, position.
Figure 2:
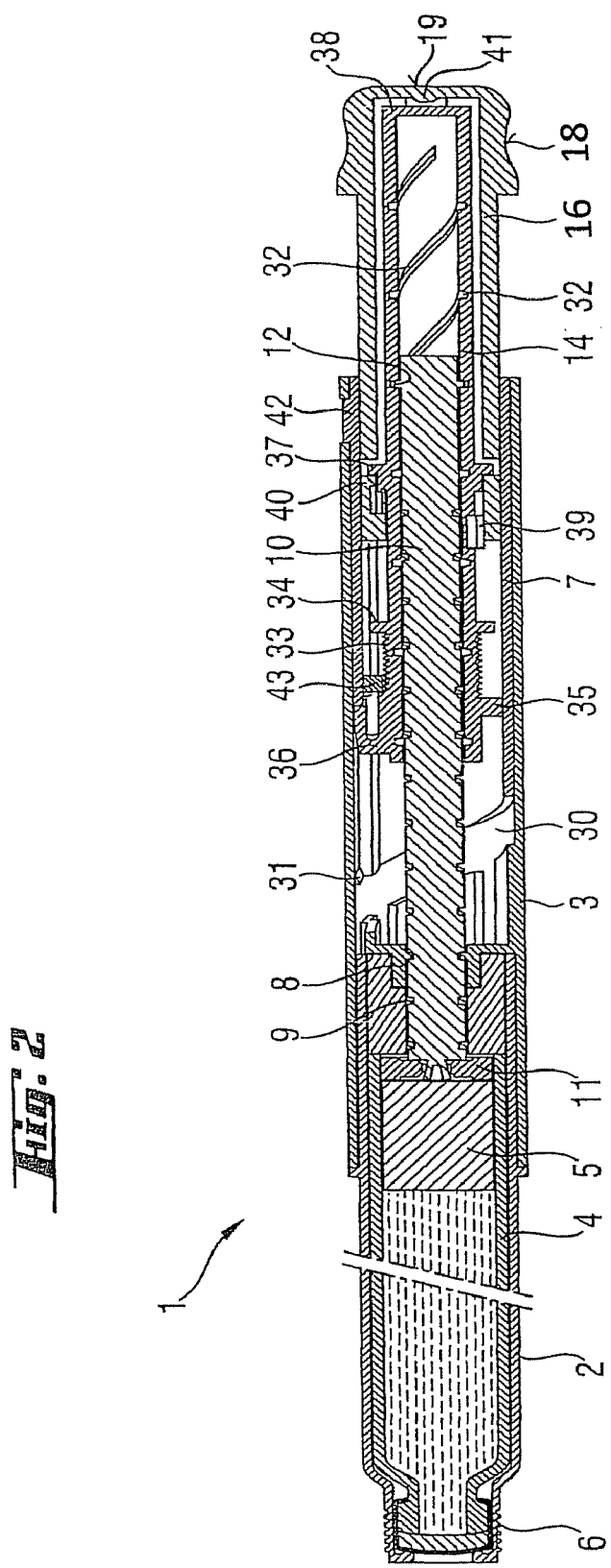
FIG. 2; shows a sectional view of an embodiment of the drug delivery device in accordance with the present invention in a second, first dose set, position.

Referring first to FIGS. 1 to 2, there is shown a drug delivery device in accordance with the present invention.

The drug delivery device (1) comprises a cartridge retaining part (2), and a main (exterior) housing part (3). The proximal end of the cartridge retaining part (2) and the distal end of the main housing (3) are secured together by any suitable means known to the person skilled in the art. In the illustrated embodiment, the cartridge retaining part (2) is secured within the distal end of the main housing part (3).

A cartridge (4) from which a number of doses of a medicinal product may be dispensed is provided in the cartridge retaining part (2). A piston (5) is retained in the proximal end of the cartridge (4).

A removable cap (not shown) is releasably retained over the distal end of the cartridge retaining part (2). The removable cap (not shown) is optionally provided with one or more window apertures (42) through which the position of the piston (5) within the cartridge (4) can be viewed.

The distal end of the cartridge retaining part (2) in the illustrated embodiment, is provided with a distal threaded region (6) designed for the attachment of a suitable needle assembly (not shown) to enable medicament to be dispensed from the cartridge (4).

In the illustrated embodiment, the main housing part (3) is provided with a threaded circular opening (8). In the illustrated embodiment the threaded circular opening (8) comprises a series of part threads rather than a complete thread. Alternatively, the threaded circular opening (8) could be formed on a separate component that can be secured against axial and/or rotational movement with respect to the main housing part (3).

The main housing part (3) is further provided with an internal housing (7). The internal housing (7) is secured against rotational and/or axial movement with respect to the main housing part (3). Additionally, the internal housing (7) has a plurality of longitudinally extending guide slots (not shown). A track (30) is formed between the internal housing (7) and the main housing part (3). In the illustrated embodiment, the track (30) consists of a helical thread portion and a linear portion extending longitudinally. The helical thread portion extends for one full rotation and the linear portion links the ends of the helical thread portion to create a continuous track. The distal end of the linear portion of the track (30) is provided with a detent feature (31). Optionally, the internal housing (7) may be transparent. Alternatively, the internal housing (7) may be formed integrally with the main housing part (3).

A first thread (9) is formed at the distal end of the piston rod (10). The piston rod (10) is of generally circular cross-section. The first thread (9) of the piston rod (10) extends through and is threadedly engaged with the threaded circular opening (8) of the main housing part (3). A pressure foot (11) is located at the distal end of the piston rod (10). The pressure foot (11) is disposed to abut the proximal face of the piston (5). A second thread (12) is formed at the proximal end of the piston rod (10). The lead of the second thread (12) of the piston rod (10) is essentially equal to the lead of the helical portion of the track (30) formed between the internal housing (7) and the main housing part (3).

The first thread (9) and the second thread (12) of the piston rod (10) are oppositely disposed.

A drive sleeve (14) extends about the piston rod (10). The drive sleeve (14) is of a generally cylindrical cross-section. A first thread (32) is formed on an internal surface of the drive sleeve (14). A flexible lug (36) is formed at the distal end of the drive sleeve (14). A first radially extending flange (35) and a second radially extending flange (34) are formed on the drive sleeve (14). A second thread (33) is formed on an external surface of the drive sleeve (14) between the first radially extending flange (35) and the second radially extending flange (34). A third radially extending flange (37) is formed proximally of the second radially extending flange (34). A radially extending pawl feature (39) is formed on the drive sleeve (14) distally of the third radially extending flange (37). A bearing face (38) is formed at the proximal end of the drive sleeve (14).

The first thread (32) of the drive sleeve (14) is engaged with the second thread (12) of the piston rod (10).

The flexible lug (36) of the drive sleeve (14) is designed to engage with the track (30) formed between the main housing part (3) and the internal housing (7).

A nut (43) is located between the drive sleeve (14) and the internal housing (7), disposed between the first flange (35) and the second flange (34). In the illustrated embodiment the nut (43) is a half-nut. This assists in the assembly of the device. The nut (43) has an internal thread that is threadedly engaged with the second thread (33) of the drive sleeve (14). The outer surface of the nut (43) and an internal surface of the internal housing (7) are keyed together by splines (not shown) to prevent relative rotation between the nut (43) and the internal housing (7), while allowing relative longitudinal movement therebetween.

The activation means (16) has a grip surface (18) and a dispensing face (19). A ratchet tooth (not shown) is formed on an internal cylindrical surface of the activation means (16). Radial inwardly projecting retention means (40) are formed on the activation means (16) and are designed to abut the distal face of the third flange (37) of drive sleeve (14).

A plurality of guide lugs (not shown) are formed on an external surface of the activation means (16). The guide lugs (not shown) are located within the guide slots (not shown) of the internal housing (7). The interaction of the guide lugs (not shown) with the guide slots (not shown) of the internal housing (7) define the extent of permissible axial movement of the activation means (16) with respect to the main housing part (3). In the illustrated embodiment the guide lugs (not shown) also prevent rotational movement of the activation means (16) relative to the main housing part (3).

A bearing point (41) is formed on an internal proximal surface of the activation means (16) and is disposed to abut the bearing face (38) of the drive sleeve (14).

To increase intuitiveness of the operation of the device, the main housing part (3) may optionally be provided with a window aperture (42) through which optional graphical status indicators, provided on the activation means (16), can be viewed.

Operation of the drug delivery device in accordance with the present invention will now be described.

To set a dose a user grips the grip surface (18) of the activation means (16). The user then pulls the activation means (16) in a proximal direction away from the main housing part (3).

As the activation means (16) moves in the proximal direction, the drive sleeve (14) is also moved in the proximal direction by virtue of the interaction between the retaining means (40) of the activation means (16) and the third flange (37) of the drive sleeve (14). As the flexible lug (36) of the drive sleeve (14) abuts the detent feature (31) of the track (30), the drive sleeve (14) is caused to rotate along the helical portion of the track (30). As the lead of the track (30) is essentially equal to the lead of the first thread (32) of the drive sleeve (14) and the second thread (12) of the piston rod (10), the piston rod (10) is not moved with respect to the main housing part (3).

The proximal travel of the activation means (16) is limited by the guide slots of the internal housing (7) a distance corresponding to one thread lead of the helical portion of the track (30). At the end of the travel of the activation means (16), the pawl feature (39) of the drive sleeve (14) engages with the ratchet tooth (not shown) of the activation means (16). As indicated in FIG. 2, by this action the drive sleeve (14) is displaced a distance equal to one lead of the first thread (32) of the drive sleeve (14) in the proximal direction relative to the piston rod (10). The action of the pawl feature (39) of the drive sleeve (14) positively engaging the ratchet tooth of the activation means (16) creates an audible and tactile feedback to the user to indicate that the dose has been set. Additionally, visual feedback regarding dose setting may optionally be indicated by a graphical status indicator, provided on the activation means (16), which can be viewed through an optional window aperture (42) in the main housing part (3).

When the dose has been set, the user may then dispense this dose by depressing the dispensing face (19) of the activation means (16). By this action the drive sleeve (14) is moved axially in the distal direction relative to the main housing part (3) by virtue of the interaction between the bearing point (41) of the activation means (16) and the bearing face (38) of the drive sleeve (14). As the pawl feature (39) of the drive sleeve (14) is engaged with the ratchet tooth of the activation means (16), the drive sleeve (14) is prevented from rotating along the helical portion of the track (30) and thus the flexible lug (36) of the drive sleeve (14) moves distally along the linear portion of the track (30). As the second thread (12) of the piston rod (10) is positively engaged with the first thread (32) of the drive sleeve (14), the piston rod (10) is caused to rotate with respect to the main housing part (3) by the axial movement of the drive sleeve (14) in the distal direction. As the piston rod (10) rotates, the first thread (9) of the piston rod (10) rotates within the threaded circular opening (8) of the main housing part (3) causing the piston rod (10) to move axially in the distal direction with respect to the main housing part (3).

The distal axial movement of the piston rod (10) causes the pressure foot (11) to bear against the piston (5) of the cartridge (4) causing a dose of medicament to be dispensed through the attached needle.

The distal travel of the activation means (16) is limited by the guide slots of the internal housing (7). Audible and tactile feedback to indicate that the dose has been dispensed is provided by the interaction of the flexible lug (36) of the drive sleeve (14) with the detent feature (31) of the track (30). Additionally, visual feedback regarding dose dispensing may optionally be indicated by a graphical status indicator, provided on the activation means (16), which can be viewed through an optional window aperture (42) in the main housing part (3).

Figure 3:
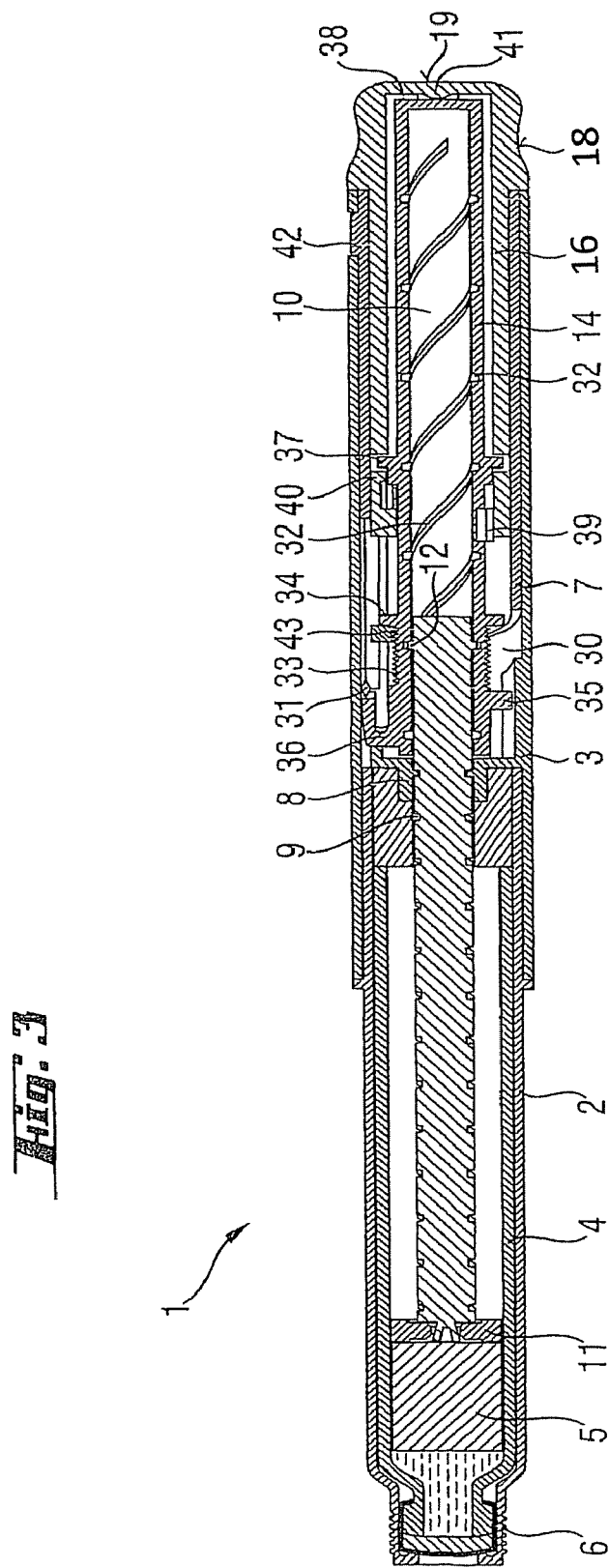
FIG. 3; shows a sectional view of an embodiment of the drug delivery device in accordance with the present invention in a third, final dose dispensed, position.

Further doses may be delivered as required up to a predetermined maximum number of doses. FIG. 3 shows the drug delivery device of instant invention in a condition where the maximum number of doses has been delivered. In this condition the nut (43) has fully traversed the second thread (33) of the drive sleeve (14) to abut the distal face of the second flange (34) of the drive sleeve (14). In this condition, the nut (43) prevents further rotational movement of the drive sleeve (14) thus preventing further doses from being selected.

The invention claimed is:

1. A drive mechanism for use in a drug delivery device, the drive mechanism comprising:
   a housing having an internal helical thread;
   an activation member that is non-rotatable with respect to the said housing;
   a drive sleeve engaged with the said housing;
   a piston rod comprising a distal threaded portion and a proximal threaded portion characterized in that,
   a) the distal threaded portion of the said piston rod is threadedly engaged with the said housing;
   b) the proximal threaded portion of the said piston rod is threadedly engaged with the drive sleeve; such that,
   c) when the said activation member moves proximally with respect to the said housing, the said drive sleeve rotates with respect to the said activation member and moves proximally with respect to the said housing;
   d) when the said activation member moves distally with respect to the said housing, the said drive sleeve (i) moves distally with respect to the said housing and (ii) is prevented from rotating with respect to the said housing, and the said piston rod is caused to rotate with respect to the said housing so that a force is transferred in the longitudinal direction to a distal end of the drug delivery device.

2. A drive mechanism according to claim 1, wherein the said piston rod is of essentially circular cross-section.

3. A drive mechanism according to claim 1, wherein the said piston rod further comprises a distal threaded portion and a proximal threaded portion wherein the said distal threaded portion and the said proximal threaded portion are oppositely disposed.

4. A drive mechanism according to claim 1, wherein the said drive sleeve is coupled with the said activation member for longitudinal travel and relative rotation between the said drive sleeve and the said activation member is allowed.

5. An assembly for use in a drug delivery device comprising the drive mechanism as defined in claim 1.

6. A drug delivery device comprising the drive mechanism as defined in claim 1.

7. The drug delivery device according to claim 6, which is a pen-type device.

8. The drug delivery device according to claim 6, which is an injector-type device.

9. The drug delivery device according to claim 6, which comprises a needle.

10. The drug delivery device according to claim 6, which is a needle-free device.

11. A method of manufacturing a drug delivery device, comprising a step of providing a drive mechanism as defined in claim 1.

12. A method of setting a dose of a medicament contained within a drug delivery device, said method comprising the steps of:
   providing a housing having an internal helical thread;
   providing a non-rotatable activation member contained within at least a portion of said housing;
   engaging a drive sleeve with said housing;
   threadedly engaging a distal thread of a piston rod with said housing;
   threadely engaging a proximal thread of said piston rod with said drive sleeve;
   moving said activation member proximally with respect to the said housing; and
   rotating said drive sleeve with respect to the said activation member wherein said drive sleeve moves proximally with respect to the said housing.

13. The method of claim 12 further comprising:
   moving said activation member distally with respect to the said housing; and
   moving said drive sleeve distally with respect to said housing wherein said drive sleeve is prevented from rotating with respect to the said housing.

14. The method of claim 13 wherein
   said drive sleeve causes said piston rod to rotate with respect to said housing so that a force is transferred in a longitudinal direction to a distal end of said drug delivery device.

15. The method of claim 12 wherein the medicament comprises a pharmaceutical formulation comprising an active compound selected from the group consisting of insulin, growth hormone, low molecular weight heparin, their analogues, and their derivatives.

* * * * *